(12) United States Patent
Jain et al.

(10) Patent No.: US 6,916,384 B2
(45) Date of Patent: Jul. 12, 2005

(54) METHOD OF TREATING A GAS SENSOR

(75) Inventors: Kailash C. Jain, Troy, MI (US); Kenneth M. Rahmoeller, West Bloomfield, MI (US); Da Yu Wang, Troy, MI (US); Paul Kikuchi, Fenton, MI (US); Carlos A. Valdes, Flint, MI (US)

(73) Assignee: Delphi Technologies, Inc., Troy, MI (US)

( * ) Notice: Subject to any disclaimer, the term of this patent is extended or adjusted under 35 U.S.C. 154(b) by 599 days.

(21) Appl. No.: 10/037,900

(22) Filed: Oct. 22, 2001

(65) Prior Publication Data

US 2003/0075440 A1 Apr. 24, 2003

(51) Int. Cl.[7] .......................... B08B 3/04; G01N 27/407
(52) U.S. Cl. ......................... 134/28; 134/29; 204/402; 204/429
(58) Field of Search ................................ 204/424, 428, 204/429, 402; 205/783.5, 785; 73/23.32; 134/26, 27, 28, 29

(56) References Cited

U.S. PATENT DOCUMENTS

| | | | |
|---|---|---|---|
| 4,136,000 A | 1/1979 | Davis et al. | |
| 4,857,165 A | * | 8/1989 | Ishiguro et al. ............. 204/424 |
| 5,271,821 A | * | 12/1993 | Ogasawara et al. ......... 204/429 |
| 5,433,830 A | | 7/1995 | Kawai et al. |
| 5,492,612 A | | 2/1996 | Kennard, III et al. |
| 6,179,989 B1 | | 1/2001 | Kennard, III et al. |
| 6,382,198 B1 | | 5/2002 | Smith et al. |
| 6,447,658 B1 | | 9/2002 | Wu et al. |
| 6,453,726 B1 | | 9/2002 | Gutierrez et al. |
| 6,514,397 B2 | | 2/2003 | LaBarge et al. |
| 6,544,467 B2 | | 4/2003 | Symons et al. |
| 6,555,159 B2 | | 4/2003 | Clyde et al. |
| 6,562,747 B2 | | 5/2003 | Symons et al. |
| 6,579,435 B2 | | 6/2003 | Wang et al. |
| 6,579,436 B2 | | 6/2003 | Wang et al. |
| 6,585,872 B2 | | 7/2003 | Donelon et al. |
| 6,616,820 B2 | | 9/2003 | Wang et al. |
| 6,638,405 B2 | | 10/2003 | Jain et al. |

* cited by examiner

Primary Examiner—Kaj K. Olsen
(74) Attorney, Agent, or Firm—Jimmy L. Funke (57) ABSTRACT

A method of treating a gas sensor comprising: disposing the gas sensor in a basic agent solution comprising a basic agent selected from the group consisting of Group IA of the Periodic Table of Elements, Group IIA of the Periodic Table of Elements, and combinations comprising at least one of the foregoing metals, wherein the gas sensor comprises an electrolyte disposed between and in ionic communication with a first electrode and a second electrode; disposing the gas sensor in an acidic agent solution; wetting at least a portion of a porous protective layer of the gas sensor with an alkaline-carbonate solution; and heating the gas sensor.

51 Claims, 11 Drawing Sheets

METHOD OF TREATING A GAS SENSOR

BACKGROUND

Automotive vehicles with an internal combustion engine have an exhaust system including a pathway for exhaust gas to move away from the engine. Depending on the desired operating state, internal combustion engines can be operated with fuel/air ratios in which (1) the fuel constituent is present in a stoichiometric surplus (rich range), (2) the oxygen of the air constituent is stoichiometrically predominant (lean range), and (3) the fuel and air constituents satisfy stoichiometric requirements. The composition of the fuel-air mixture determines the composition of the exhaust gas. In the rich range, considerable quantities of nonburned or partially burned fuel are found, while the oxygen has been substantially consumed and has nearly disappeared. In the lean range, the ratios are reversed, and in a stoichiometric composition of the fuel-air mixture, both fuel and oxygen are minimized.

It is well known that the oxygen concentration in the exhaust gas of an engine has a direct relationship to the air-to-fuel ratio of the fuel mixture supplied to the engine. As a result, gas sensors, namely oxygen sensors, are used in automotive internal combustion control systems to provide accurate oxygen concentration measurements of automobile exhaust gases for determination of optimum combustion conditions, maximization of fuel economy, and management of exhaust emissions.

A switch type oxygen sensor, generally, comprises an ionically conductive solid electrolyte material, a sensing electrode that is exposed to the exhaust gas and reference electrode that is exposed to a reference gas, such as air or oxygen, at known partial pressure. It operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right)\ln\left(\frac{P_{O_2}^{ref}}{P_{O_2}}\right)$$

where : $E$ = electromotive force
$R$ = universal gas constant
$F$ = Faraday constant
$T$ = absolute temperature of the gas
$P_{O_2}^{ref}$ = oxygen partial pressure of the reference gas
$P_{O_2}$ = oxygen partial pressure of the exhaust gas The large oxygen partial pressure difference between rich and lean exhaust gas conditions creates a step-like difference in cell output at the stoichiometric point; the switch-like behavior of the sensor enables engine combustion control about stoichiometry. Stoichiometric exhaust gas, which contains unburned hydrocarbons, carbon monoxide, and oxides of nitrogen, can be converted very efficiently to water, carbon dioxide, and nitrogen by automotive three-way catalysts in automotive catalytic converters. In addition to their value for emissions control, the sensors also provide improved fuel economy and drivability.

Further control of engine combustion can be obtained using amperometric mode exhaust sensors, where oxygen is electrochemically pumped through an electrochemical cell using an applied voltage. A gas diffusion-limiting barrier creates a current limited output, the level of which is proportional to the oxygen content of the exhaust gas. These sensors typically consist of two or more electrochemical cells; one of these cells operates in potentiometric mode and serves as a reference cell, while another operates in amperometric mode and serves as an oxygen-pumping cell. This type of sensor, known as a wide range or linear air/fuel ratio sensor, provides information beyond whether the exhaust gas is qualitatively rich or lean; it can quantitatively measure the air/fuel ratio of the exhaust gas.

Due to increasing demands for improved fuel utilization and emissions control, more recent emphasis has been on wide range oxygen sensors capable of accurately determining the oxygen partial pressure in exhaust gas for internal combustion engines operating under both fuel-rich and fuel-lean conditions. Such conditions require an oxygen sensor that is capable of rapid response to changes in oxygen partial pressure by several orders of magnitude, while also having sufficient sensitivity to accurately determine the oxygen partial pressure in both the fuel-rich and fuel-lean conditions.

The temperature of the exhaust gases ranges from ambient temperature, when the engine has not been run recently, to higher than 1,000° C. Since air-fuel ratio output signal depends largely on the exhaust gas temperature, temperature compensation is needed. A heater assists an oxygen sensor, in making more precise measurements over a wide range of exhaust gas temperatures, especially when the exhaust gas temperature is low. The addition of the heater also helps to decrease the light-off time of the sensor, that is the time that it takes for the sensor to reach the minimum temperature for proper operation.

Reduction of light-off times has been accomplished through the use of high power heaters. One method for further decreasing light-off times while using only small or modest heating power is to substantially decrease the size of the sensing element, especially the electrolyte. Similarly, during low temperature operation (e.g., about 350° C. or less), the switching time, or time required for the sensor to detect a change from rich to lean or lean to rich exhaust gas compositions, must be as low as possible, preferably below about a half second (500 milliseconds).

The internal resistance of the sensor is further factor that should be controlled. A low internal resistance or impedance will allow the sensor to sink or source more useful current from the monitoring system that is being used for determining the oxygen content of the exhaust gas.

SUMMARY

Now, according to the present disclosure, a gas sensor and a method of treating a gas sensor are described wherein the sensor is chemically cleaned and then chemically treated with an alkaline carbonate solution. One embodiment of the method comprises: disposing the gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein the gas sensor comprises an electrolyte disposed between and in ionic communication with a first electrode and a second electrode; disposing the gas sensor in an acidic agent solution; wetting at least a portion of a porous protective layer of the gas sensor with an alkaline-carbonate solution; and heating the gas sensor.

A second embodiment of the disclosed method includes a pre-treatment of a gas sensor by applying a catalytic layer to the exterior of the sensing electrode of the gas sensor. This embodiment of the method comprises: applying a catalytic layer to at least a portion of a porous protective layer of the gas sensor, the catalytic layer comprising at least one metal selected from the group consisting of palladium, platinum, rhodium, transition metals, and mixtures thereof; disposing the gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein the gas sensor comprises an electrolyte disposed between an ionic communication with a first electrode and a second electrode; disposing the gas sensor in an acidic agent solution; wetting at least a portion of a porous protective layer of the gas sensor with an alkaline-carbonate solution; and, heating the gas sensor.

A third embodiment of the disclosed method includes treating the porous protective layer of the sensing electrode of the gas sensor with a fluoride compound. According to this embodiment, the method comprises: disposing the gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein the gas sensor comprises an electrolyte disposed between an ionic communication with a first electrode and a second electrode; disposing the gas sensor in an acidic agent solution; treating at least a portion of a porous protective layer of the gas sensor with a fluoride; wetting at least a portion of the porous protective layer of the gas sensor with an alkaline-carbonate solution; and heating the gas sensor.

These and other features will be apparent from the following brief description of the drawings, detailed description, and attached drawings.

BRIEF DESCRIPTION OF THE DRAWINGS

Referring now to the following Figures, in which:

FIGS. 5–8 graphically illustrate engine performance (2.4 L twin cam–LD1) of a chemically cleaned, unheated flat-plate sensor, at exhaust gas temperature of 440° C.

FIGS. 9–10 graphically illustrate S-curve and Time response of an unheated sensor at 440° C. exhaust gas temperature on a 2.4 L LD1 engine after chemical treatment and sodium and potassium enhancement.

FIG. 20 is the time response of an unheated fluoride conditioned sensor, with heater at 0.0 V; and, FIG. 21 represents a comparison of switching characteristics of unheated flat-plate sensors at 370° C.-exhaust gas temperature on a 3.8 L V6 engine, curve (a)—a conventional electrically aged and HF treated sensor, curve (b)—a chemically treated, Pt+Rh promoted, and Na+K salt enhanced sensor according to the second embodiment disclosed herein, and curve (c)—a chemically treated, 800° C. $N_2KF$ treated, and Na+K salt enhanced sensor according to the third embodiment disclosed herein.

DETAILED DESCRIPTION

Although described in connection with an oxygen sensor, it is to be understood that the sensor, which can comprise any geometry (e.g., conical, flat plate, and the like) could be a nitrogen oxide sensor, hydrogen sensor, hydrocarbon sensor, or the like. Furthermore, while oxygen is the reference gas used in the description disclosed herein, it should be understood that other gases could be employed as a reference gas. Additionally, as used herein, unless otherwise stated, "chemically treated" or "cleaned" sensor refers to a sensor treated with both a basic agent solution and an acid agent solution; and an "non-treated", "as sintered" or "as produced" sensor refers to a sensor which did not receive electrical aging, acid, and/or basic treatment after the sintering step.

The method comprises chemically treating, subsequently treating with a mixed solution, heating the treated sensor, and washing the sensor with an alkaline solution. The resultant sensor has reduced impedance at temperatures below about 500° C., and even at temperatures below about 450° C.

Figure 1:
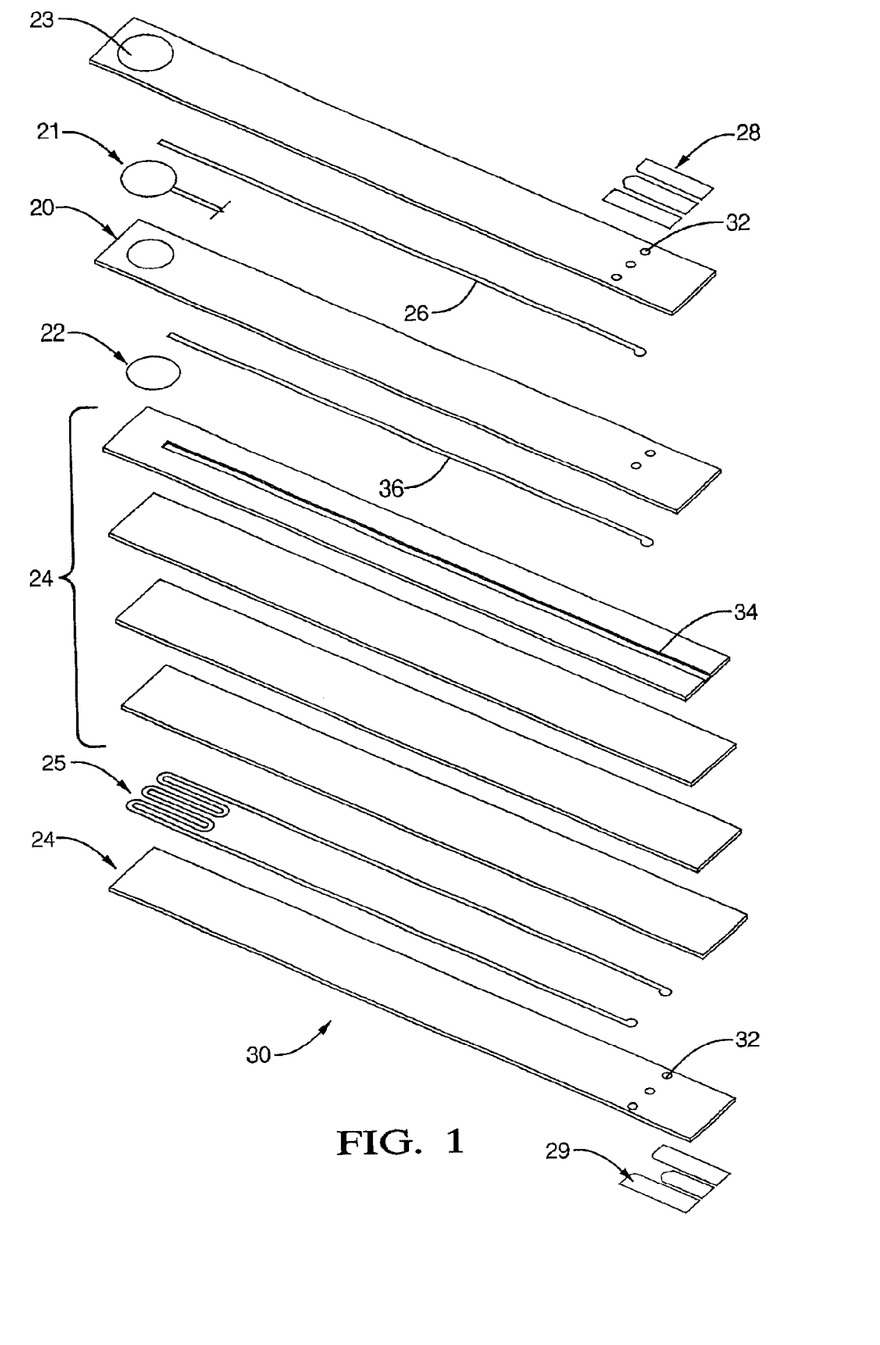
FIG. 1 is an exploded view of a general flat plate type oxygen sensor.

FIG. 1 represents one embodiment of the sensor. FIG. 1 shows a sensor (30) with an ionically conductive solid electrolyte (20), a sensing electrode (21) disposed on one side of the electrolyte (20), between the electrolyte (20) and a porous protective layer (23). On the opposite side of the electrolyte (20) is a reference electrode (22). This side of the electrolyte (20) has an insulator (24), typically alumina, containing a reference gas (e.g., air or the like) channel 34, adjacent to the electrolyte (20) such that reference air contacts electrode (22). Meanwhile, disposed across the electrolyte (20), in electrical communication with the sensing electrode (21) and the reference electrode (22), respectively, are electrical leads (26, 36). On the second side of the reference electrode (22) are support layers (24), and a heater (25). Finally, the outer sides of the sensor (30), at the end opposite the electrodes (21, 22) and electrolyte (20), are contacts (28, 29) that electrically connect to the leads (26, 36) and heater (25) through vias (32). A protective layer (not shown) may also be formed on the second side of the reference electrode (22). Additionally, other sensor components may be employed such as a pumping cell, reference chamber, lead gettering layer, ground plane, porous electrolyte, and the like, as is conventionally known in the art.

The support layers (24), heater (25), contacts (28, 29) and leads (26, 36), can be composed of materials conventionally used in exhaust sensors. For example, the support layers (24) can comprise a dielectric material such as a metal oxide, e.g., alumina, while the heater (25), contacts (28, 29) and leads (26, 36) can comprise a thermally and electrically conductive metal such as platinum, palladium, ruthenium, and the like, and other metals, metal oxides, and alloys and mixtures comprising at least one of the foregoing metals.

The solid electrolyte (20) can be formed of any material that is capable of permitting the electrochemical transfer of oxygen ions while inhibiting the passage of exhaust gases. Possible solid electrolyte materials include conventionally employed materials such as zirconia, ceria, calcia, yttria, lanthana, magnesia, and the like, as well as combinations comprising at least one of the foregoing electrolyte materials, such as yttria doped zirconia and the like.

Disposed adjacent to the solid electrolyte (20) are electrodes (21, 22). The sensing electrode (21), which is exposed to the exhaust gas during operation, preferably has a porosity sufficient to permit diffusion to oxygen molecules therethrough. Similarly, the reference electrode (22), which is typically exposed to a reference gas such as oxygen, air, or the like, during operation, preferably has a porosity sufficient to permit diffusion to oxygen molecules therethrough. These electrodes can comprise any metal capable of ionizing oxygen, including, but not limited to, noble metals such as platinum, palladium, gold, osmium, rhodium, iridium and ruthenium; and metal oxides, such as zirconia, yttria, ceria, calcia, alumina, and the like; as well as combinations comprising at least one of the foregoing metals and metal oxides. Other additives such as zirconia may be added to impart beneficial properties such as inhibiting sintering of the platinum to maintain porosity.

Disposed on the exterior side of the sensing electrode (21) is a protective layer (23) that protects the sensing electrode (21) from impurities that cause poisoning of the electrode. This protective layer typically may have a thickness ranging from about 25 to about 500 micrometers and a porosity of about 10 to about 60%. The protective coating can comprise a spinel (e.g., magnesium aluminate), alumina, zirconia, and the like, as well as combinations comprising at least one of the foregoing materials.

According to a second embodiment, the disclosed method comprises pre-treating the exterior of the sensing electrode (21) by applying a catalytic layer. The catalytic layer may be provided by applying a distinct layer of catalyst material on the porous surface of the protective layer (23) covering the outer sensing electrode (21). This catalyst layer should have porosity that is compatible with the porosity of the protective coating so as to not restrict the access of the exhaust gas to the outer electrode. This catalytic layer also may have its own porous protective coating placed over it to protect it from abrasion and/or poisoning. This coating is significantly thinner than the primary protective coating (23) over the outer electrode so as to avoid any significant "lean shift" due to portioning of hydrogen and oxygen during diffusion through it. The catalyst material may take a variety of forms. Preferably, the catalyst material is an active metal such as palladium, platinum, rhodium, and other transition metals (such as nickel, and the like), and the like, as well as alloys and combinations comprising at least one of the foregoing catalyst materials.

The catalytic layer may be formed on the sensor by depositing a catalytic material on the exposed surface of the porous protective layer (23) using thin or thick film deposition techniques. Examples of suitable thin film deposition techniques include sputtering, electron beam evaporation, chemical vapor deposition, and other similar techniques. Examples of suitable thick film deposition techniques include screen printing, pad printing, ink jet printing, and others. Other techniques such as spraying or spinning on metallo-organic solutions would also be suitable. The thickness of these thin and thick film catalytic coatings generally may range from about a few hundreds of Angstroms to about 100 micrometers, depending upon the application method and durability requirements. The durability of this catalyst layer typically improves with increasing thickness; however, it is preferred that the thickness be controlled, particularly with using thin film techniques, so as not to bridge and therefore block the pores in the protective coating and thereby preclude free access of the exhaust gas to the sensor. Preferably, the thickness of the catalytic layer is less than or equal to about 10 micrometers. It is further preferred that the thickness is greater than or equal to about 0.1 micrometers.

Thick film inks tend to develop their own porosity as they are sintered; generally, the sintering temperature should be kept low enough to prevent the formation of dense films. Porosity can be enhanced by the addition of particulate organic materials such as polymeric, microballoons, cornstarch, and other fugitive materials that burn out during sintering. Sintering of the thick films may be retarded by the addition of inorganic particulate materials that do not react with the catalytic material, such as zirconia, alumina, and other oxides, as well as combinations comprising at least one of these oxides. Cost factors may also present a factor in determining the thickness desired. Appropriate heat treatments such as sintering of the thick film or decomposition of the metallo-organic also may be preferred.

In some circumstances where extra protection of the catalytic layer from abrasion or poisoning is desirable, it may be preferred to protect this catalytic layer with an additional layer of a porous protective coating. This layer typically should be thin so as to avoid any "lean shift" caused by this layer, since the catalyst layer does not have any electrochemical function and, consequently, is less sensitive to poisoning. A suitable protective layer for this catalytic pre-equilibrium layer might be similar to the protective layer, described above, used to protect the outer electrode.

Essentially, for a planar sensor, the sensor components, e.g., electrodes (21, 22), electrolyte (20), support layers (24), heater (25), leads (26, 36), vias (32), contacts (28, 29), lead gettering layer, ground plane, porous electrolyte, pumping cell, fugitive material (reference chamber), and the like, are formed using techniques such as tape casting methods, sputtering, punching and place, spraying (e.g., electrostatically spraying, slurry spraying, plasma spraying, and the like), dipping, painting, and the like as well as combinations comprising at least one of the foregoing. The components are then laid-up in accordance with the particular type of sensor. The sensor is then heat treated to laminate the layers together. Typically, the sensor is heated to a temperature of about 1475° C. to about 1550° C. for a sufficient period of time to fully fire the layers, with a temperature of about 1490°C. to about 1510°C. preferred, for a period of up to about 3 hours or so, with about 100 minutes to about 140 minutes preferred.

The sintered sensor is subject to chemical treatments using both a basic agent and an acidic agent, preferably in sequence of a basic agent treatment followed by an acidic agent treatment. As the basic agent, an alkali or alkaline earth metal hydroxide can be employed. Possible basic agents comprises a member of Group IA of the Periodic Table of Elements ("Group IA"), Group IIA of the Periodic Table of Elements ("Group IIA"), and the like, as well as combinations comprising at least one of these hydroxides. For example, the basic agent can comprise sodium hydroxide, lithium hydroxide, magnesium hydroxide, potassium hydroxide, cesium hydroxide, barium hydroxide, strontium hydroxide, calcium hydroxide, and the like, as well as combinations comprising at least one of the foregoing basic agents, with potassium hydroxide preferred. The concentration of basic agent in the basic agent solution, which is preferably an aqueous solution, can be up to the solubility level of the basic agent, with less than or equal to about 45 weight percent (wt %) preferred, less than or equal to about 25 wt % more preferred, and less than or equal to about 20 wt % especially preferred, balance water. It is further preferred to employ a basic agent solution comprising greater than or equal to about 2 wt % basic agent, with greater than or equal to about 3 wt % basic agent more preferred, and greater than or equal to about 5 wt % basic agent especially preferred.

The acidic agent solution can comprise hydrochloric acid (HCl) in a concentration of up to the solubility level of the acidic agent, with less than or equal to about 25 wt % preferred, less than or equal to about 15 wt % more preferred, and less than or equal to about 10 wt % especially preferred, balance water. It is further preferred to employ an acidic agent solution comprising greater than or equal to about 2 wt % acidic agent, with greater than or equal to about 3 wt % acidic agent more preferred, and greater than or equal to about 4 wt % acidic agent especially preferred.

The duration of each treatment, which can be varied between several minutes and several hours, is dependent upon the concentration and temperature of the solution. The temperature of the solutions can individually range from ambient (e.g., about 25° C. or less) to boiling. In order to simplify temperature control of the solutions and process time requirements, the solutions are preferably maintained at boiling.

After the second solution treatment, at least a portion of the porous protective layer is wetted with an alkaline-carbonate solution, to treat the sensing electrode. The alkaline-carbonate solution comprises a metal hydroxide-carbonate mixture. Possible metal carbonates and metal hydroxides comprise the hydroxides (OH) and carbonates ($CO_3$) of Group I metals (e.g., sodium (Na), potassium (K), lithium (Li), and the like), Group IIa metals (e.g., calcium (Ca), magnesium (Mg), strontium (Sr), and the like), Group IIIb metals (e.g., yttrium (Y), lanthanum (La), and the like), and the like, as well as combinations comprising at least one of the foregoing hydroxides and carbonates (wherein the Groups are from the Periodic Table of Elements). For examples the alkaline-carbonate solution can comprise NaOH and $K_2CO_3$, KOH and $Na_2CO_3$, NaOH, $K_2CO_3$, KOH, and $Na_2CO_3$, and the like.

The metal hydroxide can be present in an amount of greater than or equal to about 0.1 wt. %, with greater than or equal to about 1 wt % preferred, and greater than or equal to about 2 wt % more preferred, based upon the total weight of the alkaline-carbonate solution. It is further preferred to employ less than or equal to about 15 wt. % metal hydroxide, with less than or equal to about 10 wt % metal hydroxide more preferred, and less than or equal to about 7 wt % metal hydroxide especially preferred, based upon the total weight of the alkaline-carbonate solution (e.g., metal hydroxide, metal carbonate, and solvent (e.g., water, and the like)).

The metal carbonate can be present in an amount of less than or equal to about 25 wt %, with less than or equal to about 20 wt. % preferred, and less than or equal to about 15 wt % more preferred, based upon the total weight of the alkaline-carbonate solution. It is further preferred to employ greater than or equal to about 0.15 wt % metal carbonate, with greater than or equal to about 0.5 wt % more preferred, and greater than or equal to about 2 wt % metal carbonate especially preferred.

Following the second cleaning solution treatment, and, preferably, prior to the wetting with an alkaline-carbonate solution, according to a third embodiment, the disclosed method further comprises treating at least a portion of the porous protective layer with a fluoride material. This fluoride treatment serves to assist in minimizing lean shift response times of the sensor.

An appropriate fluoride material can be: an ionic fluoride (such as lithium fluoride (LiF), sodium fluoride (NaF), potassium fluoride (KF), and the like); a covalent fluoride (such as magnesium fluoride ($MgF_2$), calcium fluoride ($CaF_2$), barium ($Ba_2$), and the like) or a fluorinating agent (such as bromine fluoride ($BrF_3$), silver fluoride ($AgF_2$), antimony fluoride ($SbF_3$), and the like); fluorides of metals; and the like, as well as combinations comprising at least one of the foregoing fluorides. Simple fluorides of metals can also be obtained by dissolving oxides, carbonates, and the like, in hydrogen fluoride (HF). Other insoluble fluorides of various elements (such as lanthanum (La), cesium (Ce), yttrium (Y), scandium (Sc), and the like) can be used as aqueous dispersions. Numerous suitable fluoride materials are available for employment with the disclosed method. Some possible fluorides materials include water-soluble fluorides (such as sodium fluoride (NaF), lithium fluoride (LiF), potassium fluoride (KF), and the like) from Group I of the Periodic Table, as well as combinations comprising at least one of the foregoing fluorides materials. In such a representative method using a fluoride solution, solutions comprising a fluoride material in an amount of greater than or equal to about 0.1 wt %, with greater than or equal to about 1 wt % preferred, based of the total weight of the solution. Also preferred is a fluoride compound amount of less than or equal to about 20 wt %, with less than or equal to about 10 wt %. An amount of fluoride of about 5 wt % is especially preferred.

The fluoride solution (aqueous or non-aqueous) may be applied in various fashions such as spraying, painting, dipping, and the like. For example, the fluoride solution can be dripped on the porous protection layer (23) covering the sensor electrode (21) and dried for about 15 minutes at about 150° C. The sensor may be heated in an oxidizing (e.g., air), a reducing (e.g., $H_2+N_2$), or a neutral atmosphere (e.g., nitrogen ($N_2$), argon (Ar), carbon dioxide ($CO_2$), and the like, and combinations comprising at least one of the foregoing neutral atmospheres). Preferably, the sensor is heated to about 600° C. to about 1,000° C., with heating to about 700° C. to about 900° C. more preferred, and heating for about one hour at about 800° C. in nitrogen atmosphere especially preferred. Following the fluoride treatment, the porous layer covering the exhaust electrode may be re-treated with an alkali metal salt solution to enhance the performance of the sensor.

Once the sensor, particularly at least a portion of the protective layer, has been treated with the mixed solution, the sensor is heated. The sensor can be heated to a temperature of up to about 1,000° C., with a temperature of about 200° C. to about 1,000° C. preferred, and a temperature of about 400° C. to about 700° C. more preferred. The period of the treatment can vary from minutes to hours, depending upon the temperature. Preferably, the period of time for the heat treatment is sufficiently long to devetrify remaining amorphous glassy layer (covering the exhaust gas electrode, electrolyte, and electrode-electrolyte interface) convert the glassy layer to an aqueous soluble layer, and incorporate small amount of salts in the sensor structure to improve electrocatalytic activity and thus sensor function.

After the heat treatment, the sensor is preferably washed, e.g., in an alkaline solution. The alkaline solution can comprise carbonates, alkalis (e.g., NaOH, ROH, LiOH, $Na_2CO_3$, and the like), or the combination thereof, of sodium, lithium, magnesium, potassium, cesium, barium, strontium, calcium, and the like, as well as combinations comprising at least one of the foregoing. The alkaline solution can be prepared from either carbonates or alkalis or their combination, for example, $Na_2CO_3$, $K_2CO_3$, NaOH, KOH, and combinations comprising at least one of the foregoing.

The concentration of the alkaline solution, as before, depends on the time and temperature of treatment. Typically, the concentration can be greater than or equal to about 1 wt % alkaline cleaner (i.e., carbonate, alkali, or combination comprising at least one of these materials), with greater than or equal to about 2 wt % preferred, balance solvent (e.g., water or the like). It is further preferred to employ less than or equal to about 20 wt % cleaner, with less than or equal to about 15 wt. % cleaner more preferred, and less than or equal to about 10 wt % cleaner especially preferred, balance solvent. For example, an about 2 wt % to about 5 wt. % boiling alkaline solution adequately washes a sensor element in up to about an hour, with about1 to about 45 minutes preferred, and about 15 to about 30 minutes more preferred. The boiling solution is used to illustrate the process as it simplifies the temperature control requirements and hot solutions work efficiently and save time.

Optionally, between the solution treatments and after the alkaline solution wash, the sensor can be rinsed with water, preferably deionized water. Finally, the sensor can be dried in a temperature ranging from ambient to a temperature that will not adversely affect the sensor components. To facilitate drying, the sensor is preferably dried at a temperature of about 700° C. to about 900° C., with a temperature of about 750° C. to about 850° C. preferred. It is further preferred to dry the sensor under an inert atmosphere (e.g., nitrogen, argon, carbon dioxide, and the like, as well as combinations comprising at least one of the foregoing inert atmospheres.

For example, a sensor can be treated with a 1 hour dip in 20 wt % basic agent (e.g., potassium hydroxide) boiling solution followed by a 3 hour dip in an acidic agent solution (e.g., $5H_2O$:1HCl) boiling solution. About 20 milligrams (mg) aqueous salt solution of sodium hydroxide and potassium carbonate can then be dripped over the porous protective layer and dried. The sensor can then treated for an hour at 600° C. After the heat treatment in air, the sensor is treated in a boiling alkaline solution. Appropriate de-ionized water rinses are employed between the various steps. The sensor can then be dried for 1 hour at 800° C. in a nitrogen atmosphere. The sequential treatment, first with an alkali followed by hydrochloric acid, then a mixed solution, heating, and finally washing with an alkaline solution, is designed to reduce the impedance of the sensor at low temperatures, e.g., below about 600° C.

Figure 2:
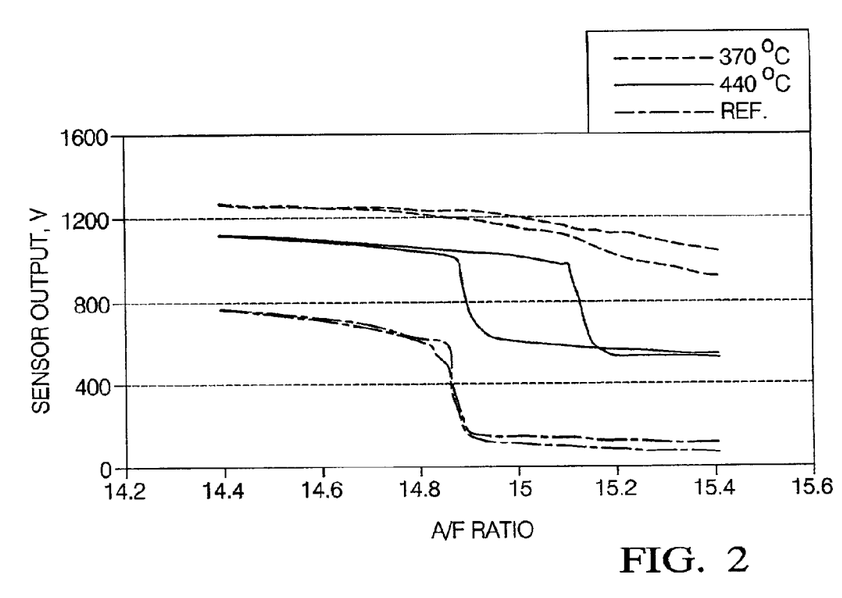
FIG. 2 is a graph showing unheated sensor output (i.e., 0 watts on the onboard heater) versus A/F ratio at low temperatures.

FIG. 2 is a graph showing sensor output versus A/F (Air/Fuel) ratio. At 370° C., and 440° C., for an unheated, untreated flat-plate type oxygen sensor versus a conical sensor (reference sensor) tested on a gas bench with standard gas feed stream. 5 microamps ($\mu$A) of oxygen was pumped into a reference electrode during measurements. As is illustrated, the electromotive force (EMF) decreases with decreasing temperature, and the switch point shifts from the stoichiometric A/F ratio (14.7) to a leaner ratio. Also, hysteresis in the response curves indicates slow and asymmetric response times for rich to lean and lean to rich transitions.

Figure 3:
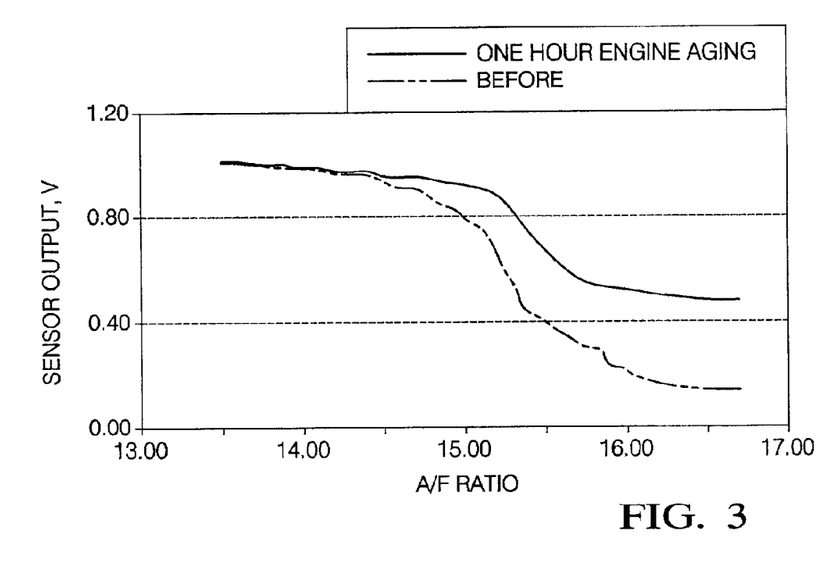
FIG. 3 illustrates S-curves and Time response of an unheated electrically aged and hydrogen fluoride treated sensors (fresh and one cycle aged) at 440° C. exhaust-gas temperature on a 2.4 L LD1 engine.
Figure 4:
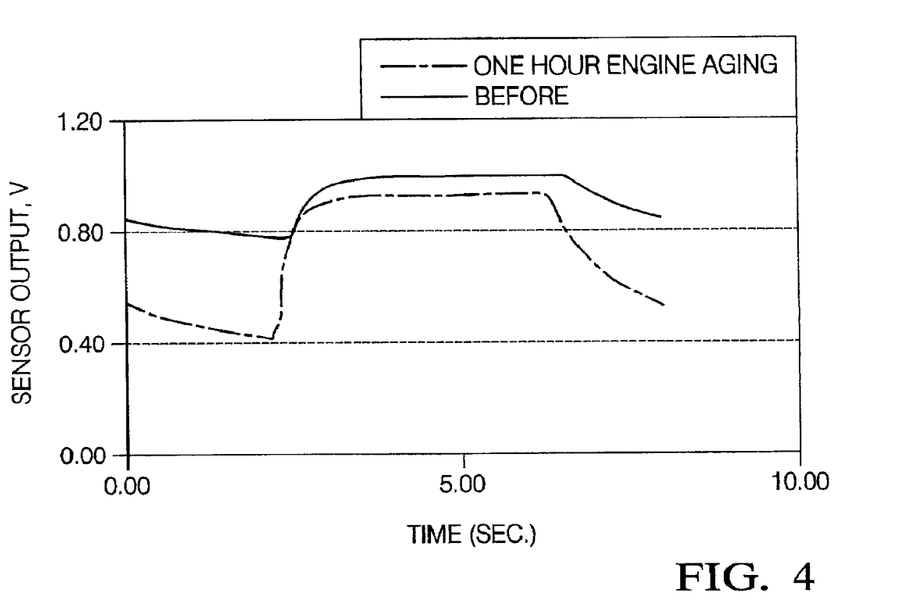
FIG. 4 illustrates sensor EMF versus Time response curves for an electrically aged and hydrogen fluoride treated oxygen sensor (fresh and one cycle aged) at 440° C. exhaust-gas temperature on a 2.4 L LD1 engine.
Figure 5:
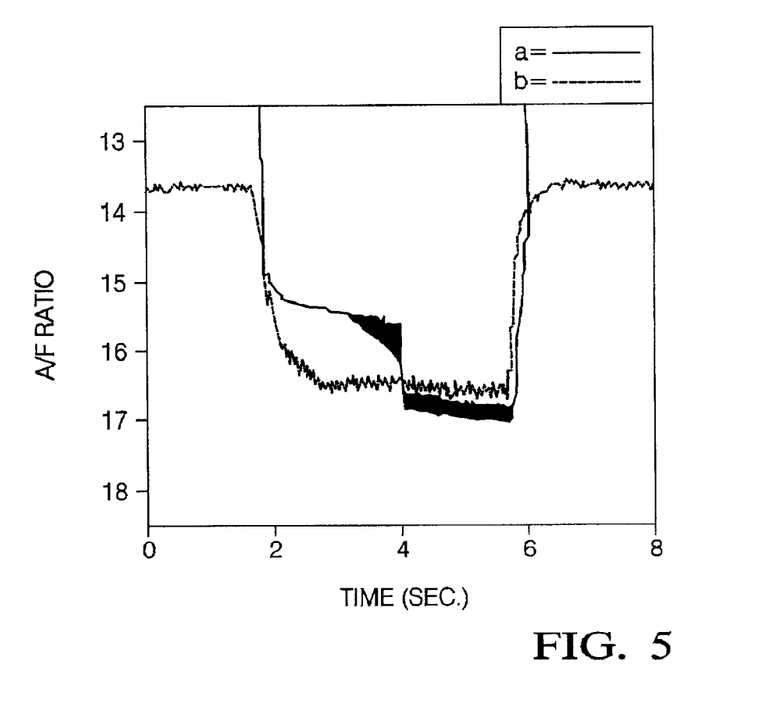
FIG. 5 shows A/F ratio vs. Time variation of exhaust gas as measured by a wide-range sensor; superimposed over the curve of the subject sensor is the curve calculated for a test sensor for the same exhaust gas.
Figure 6:
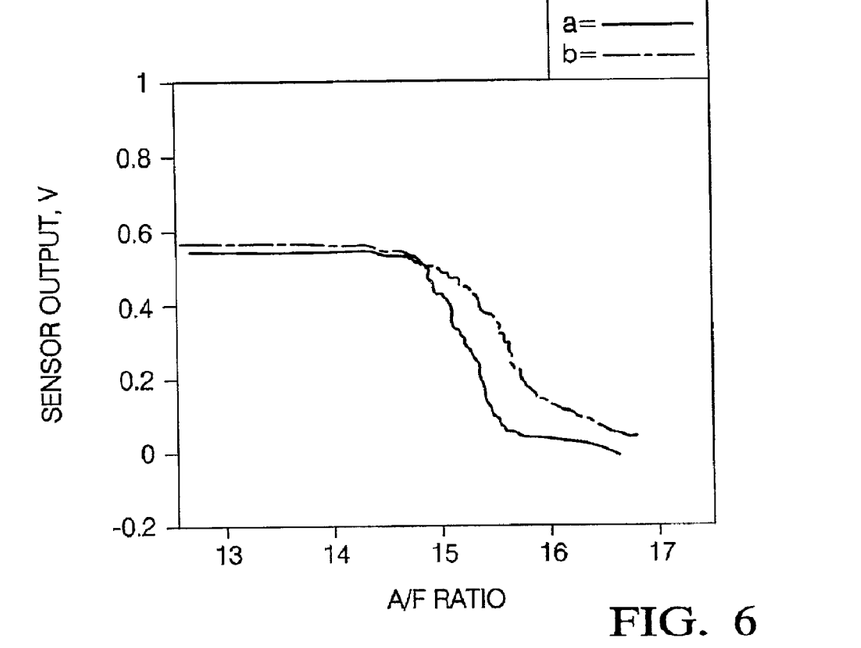
FIG. 6 illustrates Static EMF vs. Air/Fuel for the test sensor.
Figure 7:
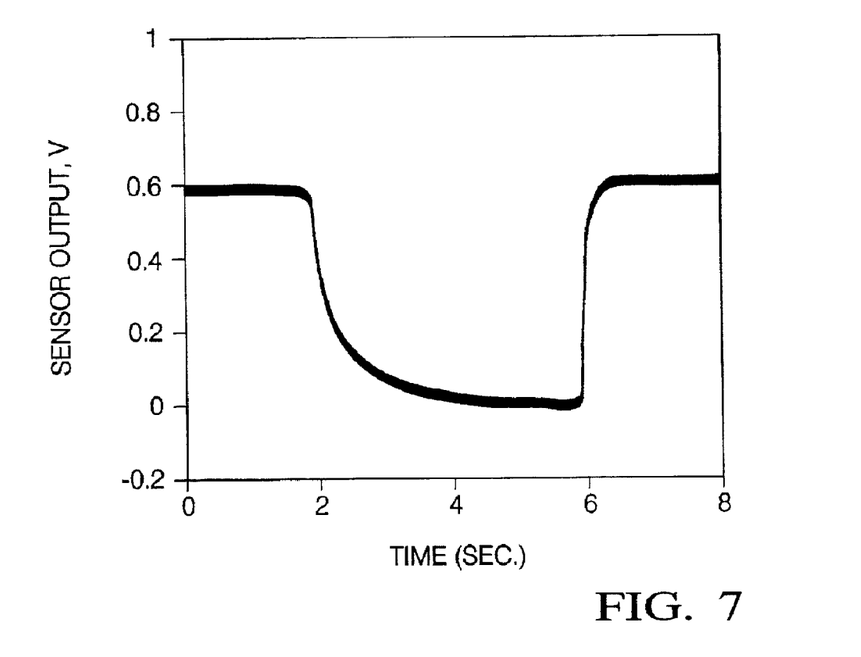
In FIG. 7, Time response EMF data on the test sensor is represented.
Figure 8:
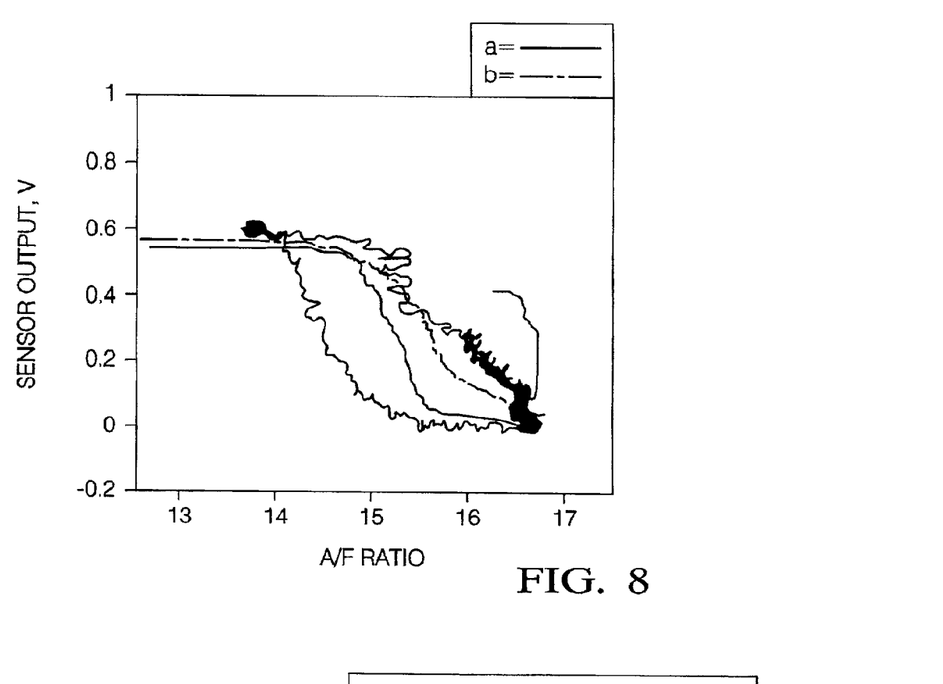
FIG. 8 shows Dynamic Response superimposed over Static Response of the sensor under test.

FIG. 3 shows the performance of an unheated standard production (electrically aged and hydrogen fluoride treated) sensor at 440° C. exhaust-gas temperature on a 2.4 L LD1 engine. "Before" refers to the S-curve of a fresh sensor and the other curve refers to measurements "After" one cycle of engine aging. The steps in the S-curves are due to noise pickup from the engine. As shown in the FIG. 3, when the onboard heater is off, the amplitude drops, lean voltage increases, and switching characteristics shift to leaner air/fuel ratios. Engine aging shifts the switching characteristics, reduces green effect, and improves the sensor amplitude. The Time response for the above sensor, FIG. 4, also improves after engine aging but the improvements are not sufficient for use as an unheated sensor.

Similar results were observed with chemically treated sensors. FIGS. 5–8, which show the engine performance (2.4 L twin cam LD1) of a chemically cleaned, unheated flat-plate sensor at 440° C. exhaust-gas temperature (Curve (a)) versus a standard wide range sensor (Curve (b)). The engine data shows that while chemical treatment substantially improves performance of as manufactured sensor elements it is not sufficient to yield sensors that perform at 440° C. exhaust-gas on the engine without an onboard heater.

Figure 9:
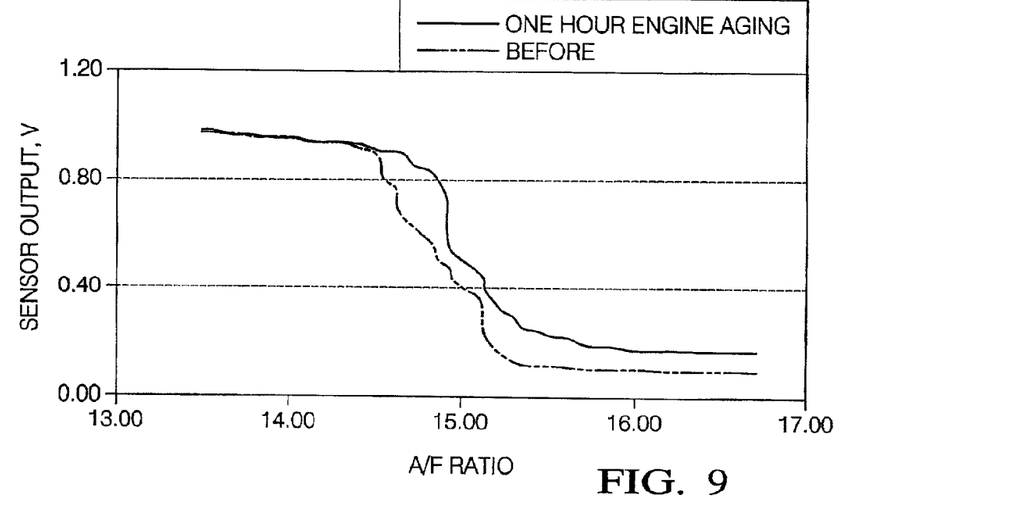
In FIG. 9, "Before" refers to S-curve of a fresh sensor and the "After" curve refers to measurements after one cycle of engine aging.
Figure 10:
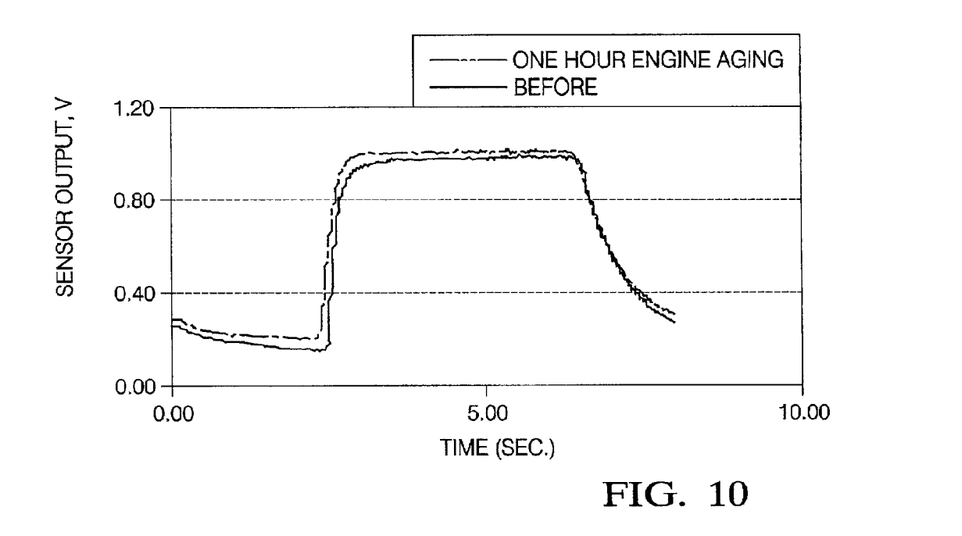
FIG. 10 depicts Time response showing lean to rich and rich to lean transitions and the effect of one cycle of engine aging.

The effect of combined chemical treatment and sodium and potassium (Na+K) salts is shown in FIGS. 9 and 10. The figures show S-curve (FIG. 9) and Time response (FIG. 10) of the sensor at 440° C. exhaust-gas temperature on a 2.4 L LD1 engine without an onboard heater. "Before" refers to S-curve of a fresh sensor and the "After" curve refers to measurements after one cycle of engine aging. The steps in the S-curves, as before, are due to noise pickup from the engine. Time response shows the lean to rich and rich to lean transitions and the effect of one cycle of engine aging. The figure shows that in comparison to standard production (a), chemically treated and salt enhanced unheated sensors (b) have proper amplitude at greater than or equal to about 440° C. exhaust gas temperature. Also, lean-shift, hysteresis in rich to lean and lean to rich transitions, and green effect is substantially reduced. Compare FIG. 3 (standard sensor) to FIG. 9 (treated sensor). In FIG. 3 the switch point is at about 15.5 A/F, in FIG. 9 it is at 15.0 A/F, so the salt treated sensor is about 0.5 A/F less lean shifted. Sensor amplitude in FIG. 3 is about 0.5 volts (V) and sensor amplitude in FIG. 9 is 0.8V. Sensor amplitude is 0.3V higher for the treated sensor. The separation between the two S-curves marked "Before" and "After" engine aging show the extent of green effect (i.e., the change in sensor characteristics upon aging on the engine) in standard sensor represented by FIG. 3. The closeness of the two S-curves in FIG. 9 shows the reduction in green effect as compared to FIG. 3. Similarly in FIG. 4 the separation in Time response curves "Before" and "After" aging on the engine shows the extent of green effect and quality of lean to rich and rich to lean transitions. As compared to FIG. 4 the separation in Time response curves before and after engine aging is minimal and FIG. 9 and FIG. 10 demonstrate substantial reduction in green effect. Consequently the light-off time is shorter.

Figure 13:
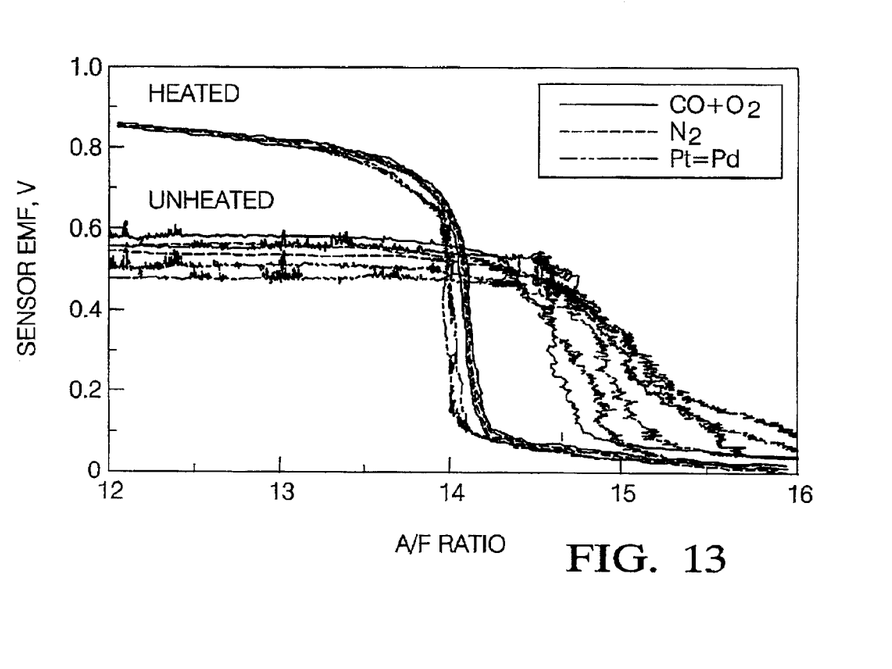
FIG. 13 shows a comparison of three heated chemically treated sensors with noble metal treatment and gas treatments at 440° C. exhaust gas temperature on a 2.4 L LD1 engine.

FIG. 13 represents a comparison of S-curves of three heated (heater at 13.5V) sensors at 440° C. exhaust gas temperature on a 2.4 L LD1 engine. Curve (1) illustrates the response of a sensor that was chemically treated and heated for an hour in nitrogen at 800° C.; Curve (2) illustrates the response of a sensor that was chemically treated and heated in carbon monoxide and oxygen ($CO/O_2$) ($O_2$ pulsed at 0.05 Hz) at 900° C.; and Curve (3) illustrates the response of a sensor that was chemically and platinum and palladium (Pt+Pd) treated and heated in nitrogen at 900° C. for one hour. S-curves of the above sensors without power on the heater (heater at 0.0 V) also are shown. This graphically demonstrates that noble metal and gas treatments alone do not accomplish stabilization of the sensor response characteristics at 440° C. exhaust gas temperature at unheated conditions (with the onboard heater at 0.0 V).

Figure 14:
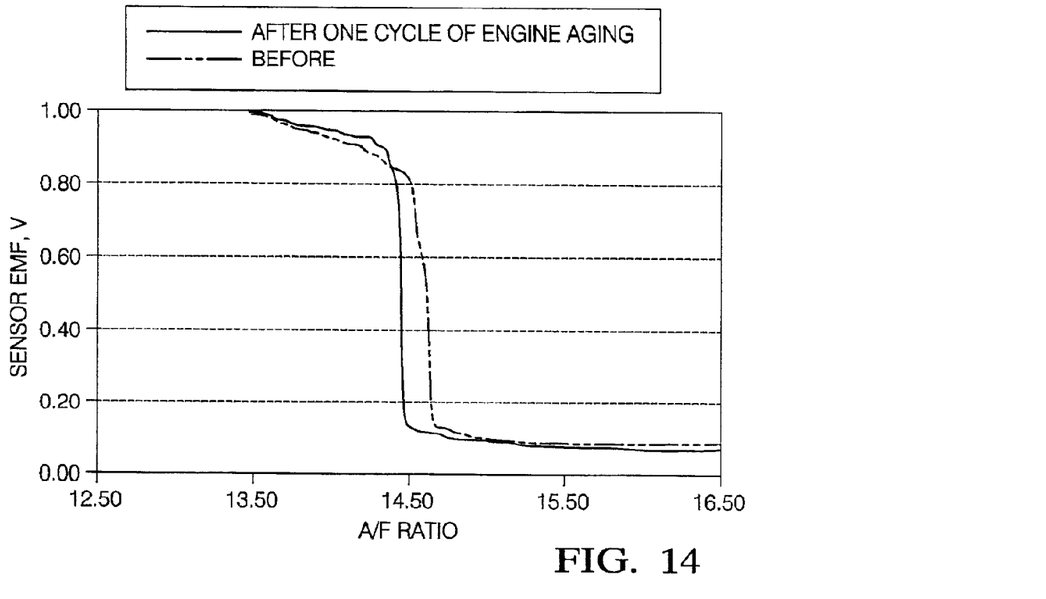
FIGS. 14 and 15 illustrate an S-curve and Time response of an unheated sensor at 440° C. exhaust gas temperature on a 2.4 L LD1 Engine after noble metal pre-treatment according to the second embodiment disclosed herein.

FIG. 14 graphically represents the performance of a sensor prepared according to the second embodiment disclosed herein, and is an S-curve of an unheated sensor at 440° C. exhaust gas temperature on a 2.4 L LD1 engine after chemical cleaning, platinum and rhodium (Pt+Rh) noble metal pre-treatment, and sodium and potassium (Na+K) enhancement. "Before" refers to S-curve of the fresh sensor and the other curve is obtained by retesting on the 2.4 L LD1 engine after one cycle of engine aging.

Figure 15:
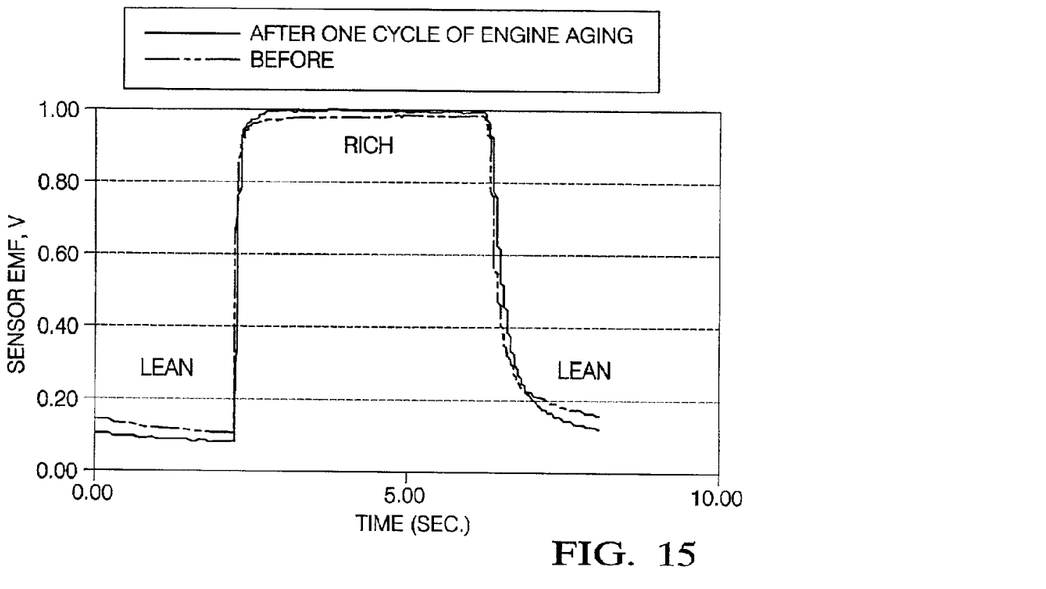

FIG. 15 is the Time response of the above sensor of FIG. 14, showing lean to rich and rich to lean transitions and the effect of one cycle of engine aging. FIGS. 14 and 15 comparatively demonstrate the extent of improvement in the amplitude, switching characteristics, and effect of aging on the engine of a sensor prepared according the method disclosed, according to the second embodiment herein, as compared to the performance of a standard production sensor, such as that represented by FIGS. 3 and 4.

Figure 16:
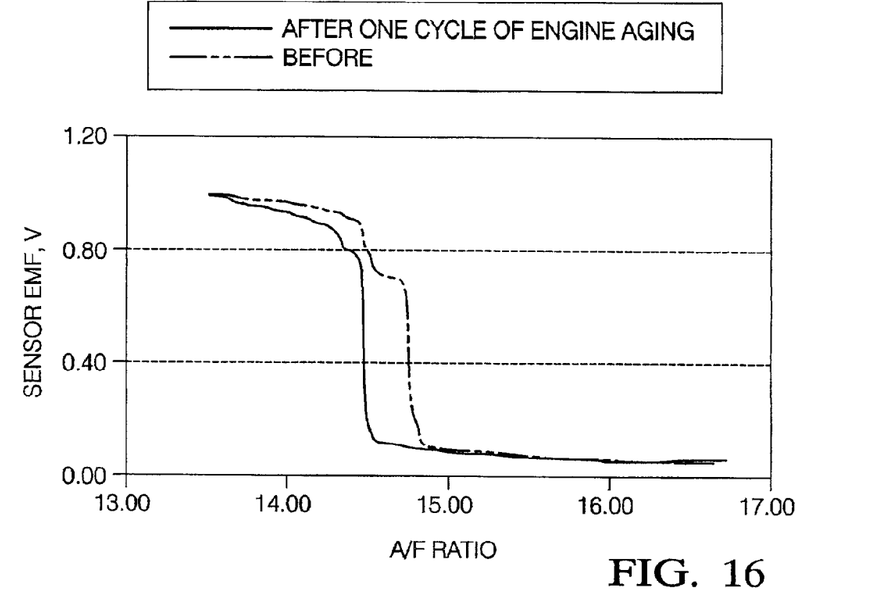
FIGS. 16 and 17 illustrate an S-curve and Time response of an unheated sensor at 440° C. exhaust gas temperature on a 2.4 L LD1 Engine after fluoride treatment according to the third embodiment disclosed herein.
Figure 17:
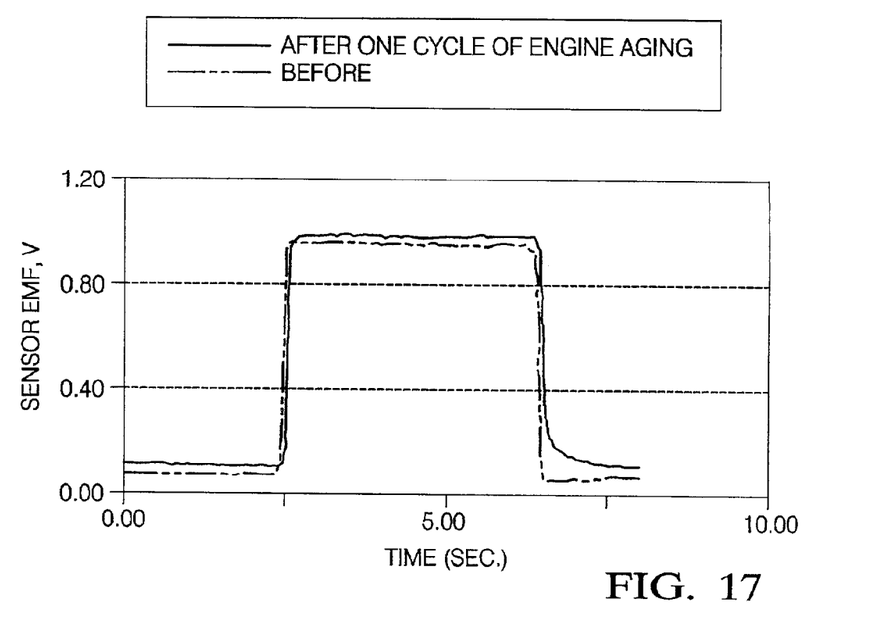

FIG. 16 is an S-curve of an unheated chemically treated and fluoride promoted sensor, according to the third embodiment herein, at 440° C. exhaust-gas temperature on a 2.4 L LD1 engine. "Before" refers to S-curve of a fresh sensor and "After" refers to S-curve after one cycle of engine aging. In FIG. 17, Time response is shown of an unheated chemically conditioned and fluoride promoted sensor, according to the third embodiment herein, at 440° C. exhaust-gas temperature on a 2.4 L LD1 engine. "Before" refers to Time response of a fresh sensor for lean to rich and rich to lean transitions and "After" refers to Time response after one cycle of engine aging. FIGS. 16 and 17 illustrate the improvements in the amplitude, switching characteristics, and effect of aging on the engine of a sensor prepared according the method disclosed, according to the third embodiment herein, as compared to the performance of a standard production sensor, such as that represented by FIGS. 3 and 4. The effect of engine aging is shown to be minimal.

Figure 11:
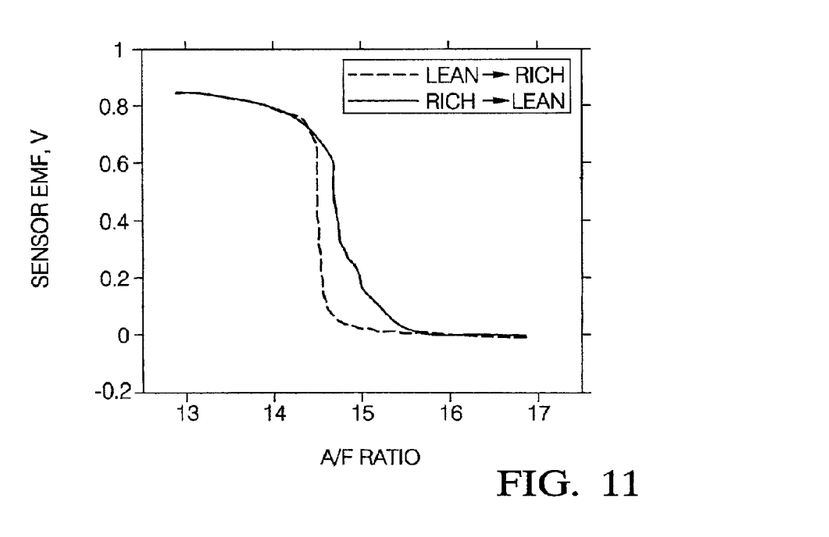
FIG. 11 graphically illustrates the operation of a standard production sensor operating with an onboard heater at 13.5 volts and at 440° C. exhaust gas temperature.
Figure 18:
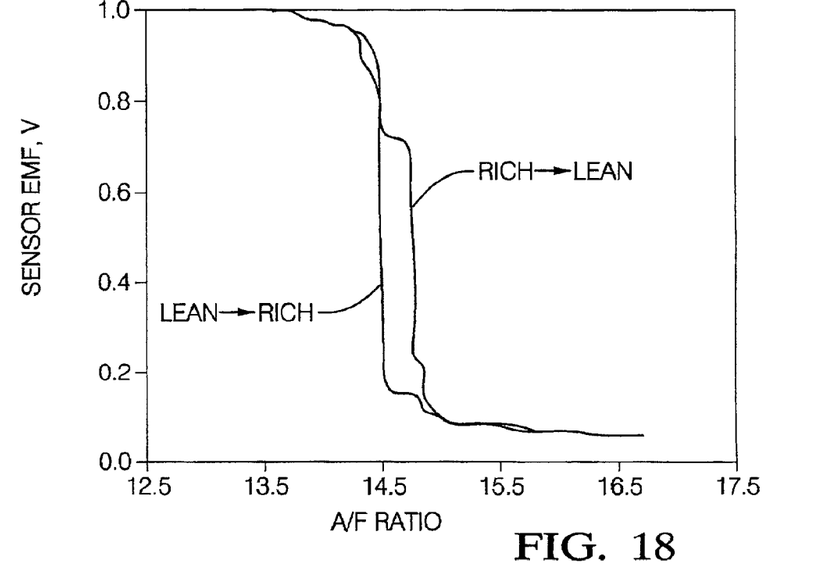
FIG. 18 shows the switching characteristics of an unheated fluoride treated sensor according to a third embodiment disclosed herein, with the heater at 0.0 V.
Figure 19:
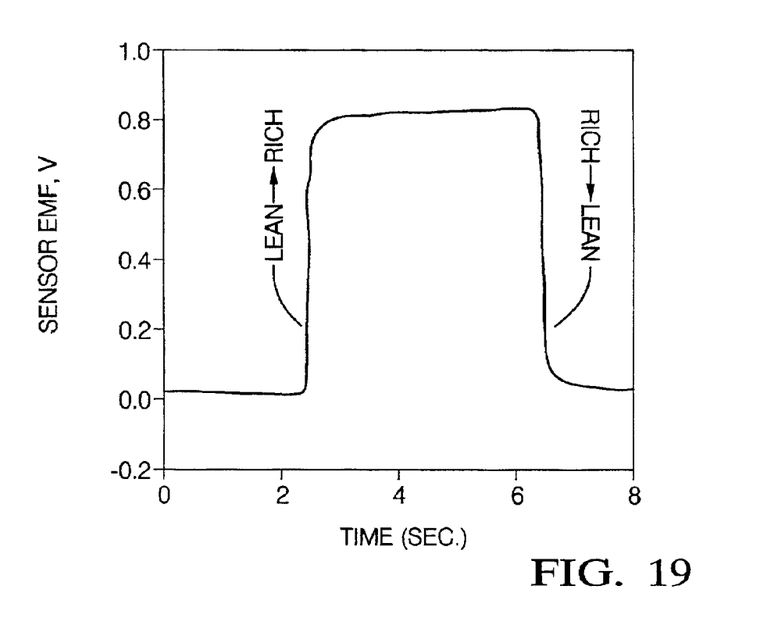
FIG. 19 is the time response of a conventional electrically aged and HF treated with heater at 13.5V sensor on a 2.4 L LD1 engine with exhaust-gas at 440° C.
Figure 20:
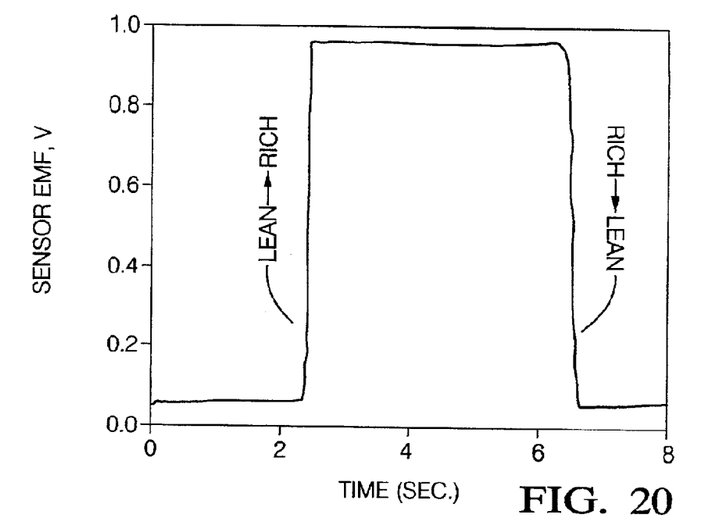

FIG. 18 shows the switching characteristics of an unheated fluoride treated sensor, according to the third embodiment herein, with a heater at 0.0V. FIG. 19 is the Time response of a conventional electrically aged and HF treated, with a heater at 13.5V, sensor on a 2.4 L LD1 engine with exhaust-gas at 440° C. FIG. 20 is the Time response of an unheated fluoride conditioned sensor, according to the third embodiment herein, with a heater at 0.0V. The performance of an unheated sensor, prepared according to the method disclosed herein, is demonstrated to be comparable to the heated (onboard heater at 13.5 V) performance of a conventional standard production sensor operated at 440° C. exhaust-gas temperature on a 2.4 L LD1 engine, as represented by FIGS. 11 and 19.

Figure 21:
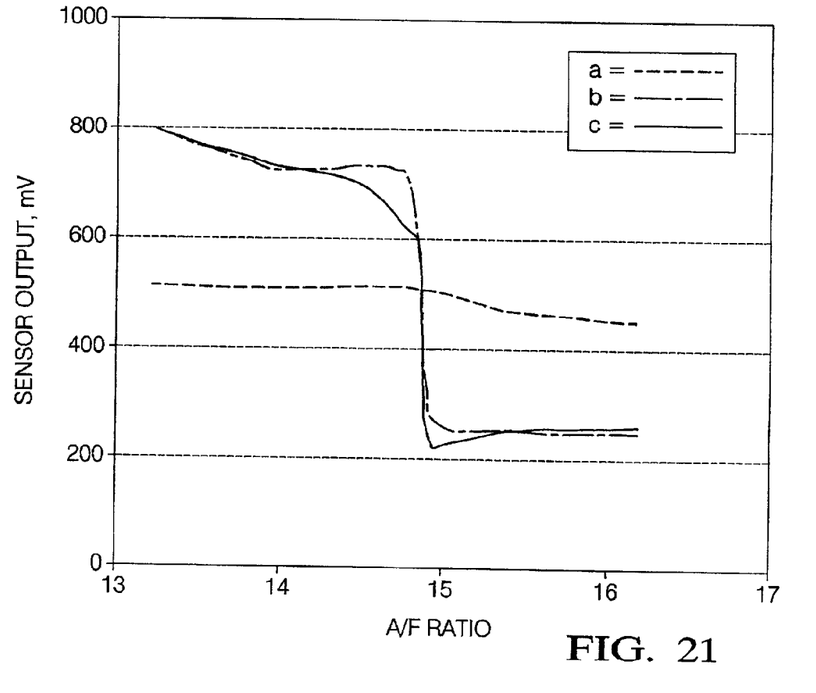

FIG. 21 represents a comparison of switching characteristics of three unheated flat-plate sensors at 370° C. exhaust gas temperature on a 3.8 L 6 valve (V6) engine. Curve (a) illustrates a standard production electrically aged and HF treated sensor; Curve (b) illustrates a chemically treated, Pt+Rh promoted, and Na+K salt enhanced sensor, prepared according to the second embodiment disclosed; and Curve (c) illustrates a chemically treated, 800° C. $N_2$ KF treated, and Na+K salt enhanced sensor, prepared according to the third embodiment disclosed herein. As clearly shown in FIG. 21, the sensors prepared according to both represented embodiments of the method disclosed are comparable to each other and markedly superior to the standard sensor.

Sensor structures are often contaminated during manufacturing processes due to sintering aids and unintentional impurities in raw materials. By the chemical treatment, especially the sequential basic agent solution followed by acidic agent solution treatment, and the mixed solution, heating, and alkaline wash, impurities are removed. The chemical treatment followed by the mixed solution, heating, and alkaline solution wash improves the sensor amplitude and eliminates sensor output voltage instabilities, high impedance, and poor switching characteristics by leaching contaminants from sensing electrode, electrolyte, sensing electrode—electrolyte interface, and the reference electrode.

Chemically treated sensors provide higher pump currents than non-treated sensors. For example, chemically treated sensors, employing at heater at 6.6 watts, have a pump current of greater than or equal to about 3 mA at 0.5 volts, with a pump current of greater than or equal to about 3.5mA at 0.5 volts preferred. Similarly, at 1 volt, with a heater at 6.6 watts, the chemically treated sensor has a pump current of greater than or equal to about 5 mA, with a pump current of greater than or equal to about 7 mA preferred, and a pump current of greater than or equal to about 8.5 mA especially preferred. In contrast, a non-treated sensor, at 1 volt, with a heater at 6.6 watts, has a pump current of less than or equal to about 1 mA.

As described above, exhaust sensors provide feed back information that is important for improving the efficiency and performance of a vehicle. The chemically treated exhaust sensor has improved accuracy, reliability, reproducibility and much reduced effect of aging on the engine also known as "green effect".

Chemical cleaning reduces the electrode impedance by a factor of 10 at 550° C. and its sensitivity to temperature and in that respect it is better or at least comparable to electrically aged and hydrofluoric acid treated sensor. Chemical cleaning, however, also improves the electrocatalytic activity of the electrode such that, at 440° C. exhaust gas temperature, the lean to rich response is 3 times and rich to lean time is 2 times improved compared to electrically aged and hydrofluoric acid treated sensors. For a control system to be useful, the sensor should have sufficiently low impedance to shorten the light-off time of the sensor especially at the initial stage of engine operation, (e.g., much less than about 1 mega-ohm (MΩ)) when the exhaust gas is still at low temperature (e.g., at about 300° C., an impedance of less than or equal to about 50 kilo-ohms (kΩ). A non-treated sensor has impedance that can exceed about 3 kΩ below 550° C. and an electrically aged and hydrofluoric acid treated sensor has impedance that can reach the same impedance at 490° C. (e.g., less than about 3 kΩ). In contrast, the chemically treated sensor has equal impedance below about 400° C. because of reduced sensitivity of electrode impedance to temperature.

In summary, by treating the sensor with chemical treatment followed by the mixed solution, heating, and alkaline wash, the performance of the sensor can be enhanced closer to a heated sensor operating at 440° C. exhaust gas temperature. The appropriate salts, carbonates, and hydroxides from Group IIa, and Y, La, and the like, can be applied to enhance sensor function. Finally, the batch nature of the process has the potential of being low-cost.

Figure 12:
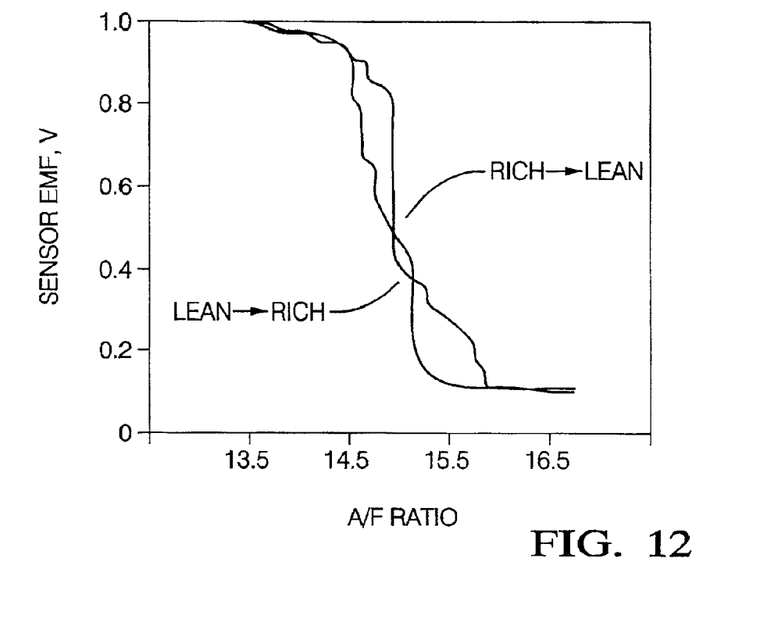
FIG. 12 graphically illustrates the operation of an unheated treated sensor (i.e., chemically treated followed by the mixed solution, heating and alkaline wash) operating at 440° C. exhaust gas temperature.

The process improves electrode electrochemical activity, sensor output amplitude, removes excess salts, maintains porosity of porous protection layer, removes glassy phase to clean the electrode, devitrifies the glassy layer, deglazes the electrode of glassy layer formed after high temperature (e.g., about 1500° C.) sintering, deactivates glassy layer so that exhaust gases can reach the electrode (e.g., the platinum electrode), increases the catalytic activity by incorporating small amounts in the structure of the sensor, and reduces sensor light-off time in an engine exhaust gas environment by removing excess salts, decomposition residues, and reaction products. The performance of the unheated sensor prepared according to the disclosed method (e.g., FIG. 12 and FIG. 16) at 440° C. exhaust gas temperature is now comparable to a standard production sensor operating with an onboard heater at 13.5V at the same exhaust gas temperature (FIG. 11).

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for treating a gas sensor, comprising:
    disposing said gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein said gas sensor comprises an electrolyte disposed between and in ionic communication with a first electrode and a second electrode;
    disposing said gas sensor in an acidic agent solution;
    wetting at least a portion of a porous protective layer of said gas sensor with an alkaline-carbonate solution; and
    heating said gas sensor, and
    following said heating, washing said gas sensor in an alkaline solution.

2. The method of claim 1, further comprising heating said basic agent solution and said acidic agent solution to boiling temperatures.

3. The method of claim 1, wherein said acidic agent solution comprises hydrochloric acid.

4. The method of claim 1, wherein said basic agent solution comprises about 2 wt % to about 45 wt % basic agent, balance water.

5. The method of claim 4, wherein said basic agent solution comprises about 3 wt % to about 25 wt % basic agent.

6. The method of claim 5, wherein said basic agent solution comprises about 5 wt % to about 20 wt % basic agent.

7. The method of claim 1, wherein said acidic agent solution comprises about 2 wt % to about 25 wt % acidic agent, balance water.

8. The method of claim 7, wherein said acidic agent solution comprises about 3 wt % to about 15 wt % acidic agent.

9. The method of claim 8, wherein said acidic agent solution comprises about 4 wt % to about 10 wt % acidic agent.

10. The method of claim 1, further comprising rinsing said gas sensor in water after disposing said gas sensor in said basic agent solution and before disposing said gas sensor in said acidic agent solution.

11. The method of claim 1, wherein said gas sensor comprises an electrode impedance of less than or equal to about 100 ohms at 550° C.

12. The method of claim 11, wherein said electrode impedance is less than or equal to about 50 ohms at 550° C.

13. The method of claim 1, wherein said gas sensor has a pump current of greater than or equal to about 3 mA at 0.5 volts with a heater at 6.6 watts.

14. The method of claim 13, wherein said gas sensor has a pump current of greater than or equal to about 3.5 mA at 0.5 volts with a heater at 6.6 watts.

15. The method of claim 1, wherein said gas sensor has a pump current of greater than or equal to about 5 mA at 1 volt with a heater at 6.6 watts.

16. The method of claim 15, wherein said gas sensor has a pump current of greater than or equal to about 7 mA at 1 volt with a heater at 6.6 watts.

17. The method of claim 16, wherein said gas sensor has a pump current of greater than or equal to about 8.5 mA at 1 volt with a heater at 6.6 watts.

18. The method of claim 1, wherein said alkaline-carbonate solution comprises a metal hydroxide-carbonate mixture.

19. The method of claim 18, wherein said metal hydroxide-carbonate mixture further comprises hydroxides and carbonates of metals selected from the group consisting of Group I metals, Group IIa metals, Group IIIb metals, and combinations comprising at least one of the foregoing.

20. The method of claim 19, wherein said metal hydroxide-carbonate mixture further comprises hydroxides and carbonates of metals selected from the group consisting of sodium, potassium, lithium, calcium, magnesium, cerium, yttrium, lanthanum, and combinations comprising at least one of the foregoing.

21. The method of claim 18, wherein an amount of metal hydroxide in said metal hydroxide-carbonate mixture is about 0.1 wt % to about 15 wt %, based upon the total weight of said metal hydroxide-carbonate mixture.

22. The method of claim 21, wherein said amount of said metal hydroxide is about 1 wt % to about 10 wt %, based upon the total weight of said metal hydroxide-carbonate mixture.

23. The method of claim 22, wherein said amount of said metal hydroxide is about 2 wt % to about 7 wt %, based upon the total weight of said metal hydroxide-carbonate mixture.

24. The method of claim 18, wherein an amount of metal carbonate in said metal hydroxide-carbonate mixture is about 0.15 wt % to about 25 wt %, based upon the total weight of said metal hydroxide-carbonate mixture.

25. The method of claim 24, wherein said amount of said metal carbonate is about 0.5 wt % to about 20 wt %, based upon the total weight of said metal hydroxide-carbonate mixture.

26. The method of claim 25, wherein said amount of said metal carbonate is about 2 wt % to about 15 wt %, based upon the total weight of said metal hydroxide-carbonate mixture.

27. The method of claim 1, wherein said alkaline solution comprises an alkaline cleaner selected from the group consisting of carbonates, alkalis, and combinations comprising at least one of the foregoing alkaline cleaners.

28. The method of claim 1, wherein said alkaline solution comprises about 1 wt % to about 20 wt % of an alkaline cleaner.

29. The method of claim 28, wherein said alkaline solution comprises about 2 wt % to about 15 wt % of the alkaline cleaner.

30. The method of claim 1, further comprising heating said alkaline solution to a boiling temperature.

31. The method of claim 1, wherein said heating said gas sensor comprises heating said gas sensor to a temperature of about 200° C. to about 1,000° C.

32. The method of claim 31, wherein said temperature is about 400° C. to about 700° C.

33. The method of claim 1, wherein said basic agent is selected from the group consisting of sodium hydroxide, lithium hydroxide, magnesium hydroxide, potassium hydroxide, cesium hydroxide, barium hydroxide, strontium hydroxide, calcium hydroxide, and combinations comprising at least one of the foregoing basic agents.

34. The method of claim 1, further comprising pre-treating and porous protective layer by applying a catalytic layer comprising at least one metal selected from the group consisting of palladium, platinum, rhodium, transition metals, and combinations comprising at least one of the foregoing metals.

35. The method of claim 34, comprising applying said catalytic layer to a thickness ranging from about 100 Angstroms to about 100 micrometers.

36. The method of claim 35, comprising applying said catalytic layer to a thickness of about 0.1 to about 10 micrometers.

37. The method of claim 34, further comprising applying said catalytic layer by a thin film deposition technique selected from the group consisting of sputtering, electron beam evaporation, chemical vapor deposition, and combinations comprising at least one of the foregoing techniques.

38. The method of claim 34, further comprising applying said catalytic layer by a thick film deposition technique selected from the group consisting of screen printing, pad printing, ink jet printing, spraying or metallic-organism solutions, and combinations comprising at least one of the foregoing techniques.

39. The method of claim 1, further comprising treating at least a portion of a porous protective layer of said gas sensor with a fluoride material, subsequent to disposing said gas sensor in an acidic agent solution.

40. The method of claim 39, wherein said fluoride material is selected from the group consisting of ionic fluorides, covalent fluorides, fluorinating agents, and combinations comprising at least one of the foregoing fluoride materials.

41. The method of claim 39, wherein said fluoride material is applied by wetting at least a portion of said porous protective layer with a fluoride solution.

42. The method of claim 41, wherein said aqueous fluoride solution comprises a solution of a fluoride of a Group I element of the Periodic Table of Elements.

43. The method of claim 41, wherein said fluoride solution comprises about 0.1 wt % to about 20 wt % of said fluoride material.

44. The method of claim 43, wherein said fluoride solution comprises about 1 wt % to about 10 wt % of said fluoride material.

45. The method of claim 41, further comprising heating the fluoride treated gas sensor to a temperature of about 600° C. to about 1,000° C.

46. The method of claim 45, wherein said temperature is about 700° C. to about 900° C.

47. The method of claim 41, wherein said treating with a fluoride solution is applied prior to wetting the porous protective layer with an alkaline-carbonate solution.

48. The method of claim 41, wherein said fluoride solution is an aqueous fluoride solution.

49. A method for treating a gas sensor, comprising:
applying a catalytic layer to at least a portion of a porous protective layer of said gas sensor, said catalytic layer comprising a selected from the group consisting of palladium, platinum, rhodium, transition metals, and combinations comprising at least one of the foregoing metals;
disposing said gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein said gas sensor comprises an electrolyte disposed between an ionic communication with a first electrode and a second electrode;
disposing said gases sensor in an acidic agent solution;
wetting at least a portion of a porous protective layer of said gas sensor with an alkaline-carbonate solution;
heating said gas sensor; and
following said heating, washing said sensor in an alkaline solution.

50. A method for treating a gas sensor comprising:
disposing said gas sensor in a basic agent solution comprising a basic agent comprising an element selected from the group consisting of Group IA of the Periodic Table of Elements, Group IIA of the Periodic Table of Elements, and combinations comprising at least one of the foregoing elements, wherein said gas sensor comprises an electrolyte disposed between an ionic communication with a first electrode and a second electrode;
disposing said gas sensor in an acidic agent solution;
treating at least a portion of a porous protective layer of said gas sensor with a fluoride material;
wetting at least a portion of a porous protective layer of said gas sensor with an alkaline-carbonate solution; and
heating said gas sensor.

51. The method of claim 50, further comprising washing said gas sensor in an alkaline solution, following said heating of said gas sensor.

* * * * *